(12) United States Patent
Huang et al.

(10) Patent No.: US 8,338,392 B2
(45) Date of Patent: Dec. 25, 2012

(54) MICRORNA MODULATORS AND METHOD FOR IDENTIFYING AND USING THE SAME

(75) Inventors: Qihong Huang, Philadelphia, PA (US); Alexander Deiters, Raleigh, NC (US); Kiranmai Gumireddy, Philadelphia, PA (US)

(73) Assignees: The Wistar Institute, Philadelphia, PA (US); North Carolina State University, Raleigh, NC (US)

( * ) Notice: Subject to any disclaimer, the term of this patent is extended or adjusted under 35 U.S.C. 154(b) by 0 days.

(21) Appl. No.: 12/918,183

(22) PCT Filed: Feb. 20, 2009

(86) PCT No.: PCT/US2009/034611
§ 371 (c)(1),
(2), (4) Date: Aug. 18, 2010

(87) PCT Pub. No.: WO2010/051048
PCT Pub. Date: May 6, 2010

(65) Prior Publication Data
US 2010/0317628 A1    Dec. 16, 2010

Related U.S. Application Data

(60) Provisional application No. 61/029,971, filed on Feb. 20, 2008, provisional application No. 61/110,101, filed on Oct. 31, 2008.

(51) Int. Cl.
| | |
|---|---|
| *A01N 33/26* | (2006.01) |
| *A01N 37/18* | (2006.01) |
| *A01N 33/18* | (2006.01) |
| *A01N 33/24* | (2006.01) |
| *A61K 31/655* | (2006.01) |
| *A61K 31/16* | (2006.01) |
| *A61K 31/04* | (2006.01) |

(52) U.S. Cl. .................. 514/150; 514/615; 514/741
(58) Field of Classification Search .................. None
See application file for complete search history.

(56) References Cited

U.S. PATENT DOCUMENTS

| | | | |
|---|---|---|---|
| 2005/0261218 A1 | 11/2005 | Esau et al. | 514/44 A |
| 2007/0099876 A1 | 5/2007 | Forster | 514/150 |
| 2008/0318995 A1 | 12/2008 | Cushman et al. | 514/284 |

FOREIGN PATENT DOCUMENTS

WO    WO 2004/106358 A1    12/2004

OTHER PUBLICATIONS

Morley "Theoretical investigation of the electronic properties of donor-acceptor N-benzylideneanilines and related molecules", J.Chem.Soc.PerkinTrans.2, 1995, vol. 4, pp. 731-734.*

Xiao et al. "On the Binding of Indeno[1,2-c]isoquinolines in the DNA-Topoisomerase I Cleavage Complex", J.Med.Chem., 2005, vol. 48, pp. 3231-3238.*
Singer et al., "Second-order nonlinear-optical properties of donor- and acceptor-substituted aromatic compounds", J. Opt. Soc. Am. B., 1989, vol. 6, No. 7, pp. 1339-1350.*
Chan et al. "MicroRNA-21 is an Antiapoptotic Factor in Human Glioblastoma Cells" Cancer Research 2005 65(14):6029-6033.
Cheng et al. "Antisense Inhibition of Human miRNAs and Indications for an Involvement of miRNA in Cell Growth and Apoptosis" Nucleic Acids Research 2005 33(4):1290-1297.
Ciafrè et al. "Extensive Modulation of a Set of MicroRNAs in Primary Glioblastoma" Biochemical and Biophysical Research Communications 2005 334:1351-1358.
Cimmmino et al. "*miR-15* and *miR-16* Induce Apoptosis by Targeting BCL2" Proceedings of the National Academy of Sciences USA 2005 102(39):13944-13949 with Correction PNAS 2006 103(7):2464-2465.
Enginar et al. "Synthesis of $^{131}$I Labeled Estrone Derivatives and Biodistribution Studies on Rats" Journal of Radioanalytical and Nuclear Chemistry 2005 264(3):535-539.
Hayashita et al. "A Polycistronic MicroRNA Cluster, *miR-17-92*, Is Overexpressed in Human Lung Cancers and Enhances Cell Proliferation" Cancer Research 2005 65(21):9628-9632.
He et al. "A MicroRNA Polycistron as a Potential Human Oncogene" Nature 2005 435(9):828-833.
Holt et al. "Steroidal a Ring Aryl Carboxylic Acids: A New Class of Steroid 5α-Reductase Inhibitors" Journal of Medicinal Chemistry 1990 33:937-942.
Huang et al. "The MicroRNAs miR-373 and miR-520c Promote Tumour Invasion and Metastasis" Nature Cell Biology 2008 10(2):202-210 with Supplementary Information 1-15.
Lusic et al. "Photochemical DNA Activation" Organic Letters 2007 9(10):1903-1906.
Meister et al. "Human Argonaute2 Mediates RNA Cleavage Targeted by miRNAs and siRNAs" Molecular Cell 2004 15:185-197.
Strumberg et al. "Synthesis of Cytotoxic Indenoisoquinoline Topoisomerase I Poisons" Journal of Medicinal Chemistry 1999 42:446-457.
Tam, W. and Dahlberg, J. E. "miR-155/*BIC* as an Oncogenic MicroRNA" Genes, Chromosomes & Cancer 2006 45:211-212.
Thum et al. "MicroRNA-21 Contributes to Myocardial Disease by Stimulating MAP Kinase Signalling in Fibroblasts" Nature 2008 456(18):980-986.
Zhang et al. "MicroRNAs Exhibit High Frequency Genomic Alterations in Human Cancer" Proceedings of the National Academy of Sciences USA 2006 103(24):9136-9141.

* cited by examiner

Primary Examiner — James D Anderson
Assistant Examiner — Stephanie Springer
(74) Attorney, Agent, or Firm — Licata & Tyrrell P.C.

(57) ABSTRACT

The present invention is a method for identifying agents which modulate microRNA activity. The invention involves contacting a cell harboring a microRNA and a microRNA binding sequence, which is operably linked to a nucleic acid molecule encoding a reporter protein, with a test agent increases or decreases the expression of the reporter protein thereby identifying a microRNA modulator. Antagonists identified by this screening assay are provided, as are methods for using the same to inhibit microRNA activity and prevent or treat disease.

2 Claims, 4 Drawing Sheets

SEQUENCE LISTING

<160> NUMBER OF SEQ ID NOS: 24

<210> SEQ ID NO 1
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 1
gagcuacagu gcuucaucuc a        21

<210> SEQ ID NO 2
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 2
ucaguuuugc auagauuugc aca        23

<210> SEQ ID NO 3
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 3
cccuccacca ugcaagggau g        21

<210> SEQ ID NO 4
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 4
aacccaugga auucaguucu ca        22

<210> SEQ ID NO 5
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 5
ccacacacuu ccuuacauuc ca        22

<210> SEQ ID NO 6
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 6
cagacuccgg uggaaugaag ga        22

```
<210> SEQ ID NO 7
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 7
ucaacaucag ucugauaagc ua                                                  22

<210> SEQ ID NO 8
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 8
uccacaugga guugcuguua ca                                                  22

<210> SEQ ID NO 9
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 9
cacugguaca aggguuggga ga                                                  22

<210> SEQ ID NO 10
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 10
ucauagcccu guacaaugcu gcu                                                 23

<210> SEQ ID NO 11
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 11
aguacaucau cuauacugua                                                     20

<210> SEQ ID NO 12
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 12
agggauuccu gggaaaacug gac                                                 23

<210> SEQ ID NO 13
<211> LENGTH: 22
<212> TYPE: RNA
<213> ORGANISM: Artificial sequence
<220> FEATURE:
<223> OTHER INFORMATION: Synthetic oligonucleotide
```

```
<400> SEQUENCE: 13
uagcuuauca gacugauguu ga                                              22

<210> SEQ ID NO 14
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 14
cuuucagucg gauguuugca gc                                              22

<210> SEQ ID NO 15
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 15
tttaatggcc ttgcactctt ctt                                             23

<210> SEQ ID NO 16
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 16
tttgttccag tattaggagc tgttttt                                         27

<210> SEQ ID NO 17
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 17
cgacatgaac ggctgttact ca                                              22

<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
ttgctcacct tgcggttct                                                  19

<210> SEQ ID NO 19
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 19
aaatctgaaa gcggctgata ctg                                             23
```

```
<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
cggaaccgct tccttcatag                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
ccgttggaag gaagctacca                                              20

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
cgtactgctg gatgctgatg a                                            21

<210> SEQ ID NO 23
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 23
ctgagccaga ttacaggaat gaag                                         24

<210> SEQ ID NO 24
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 24
gaacttgtgc aaaccaatat aagatctaa                                    29
```

MICRORNA MODULATORS AND METHOD FOR IDENTIFYING AND USING THE SAME

This application claims benefit of priority from PCT/US2009/034611, filed Feb. 20, 2009, and U.S. Provisional Patent Application Ser. Nos. 61/029,971, filed Feb. 20, 2008, and 61/110,101, filed Oct. 31, 2008, the contents of which are incorporated herein by reference in their entireties.

BACKGROUND OF THE INVENTION

MicroRNAs (miRNAs) are single-stranded noncoding RNAs of ~22 nucleotides. They are a novel class of gene regulators that function by binding to the 3' untranslated region of target messenger RNAs leading to either suppression of their translation or acceleration of their degradation (Bartel (2004) *Cell* 116:287; Carthew (2006) *Curr. Opin. Genet. Dev.* 16:203; He & Hannon (2004) *Nat. Rev. Genet.* 5:522; Cullen (2004) *Mol. Cell.* 16:861; Du & Zamore (2005) *Development* 132:4645). The majority of miRNAs are initially transcribed by RNA polymerase II as primary transcripts (pri-miRNAs) that require subsequent processing to yield a functional mature miRNA (Bartel (2004) supra; Carthew (2006) supra; He & Hannon (2004) supra; Cullen (2004) supra; Du & Zamore (2005) supra). Pri-miRNAs are processed in the nucleus by the RNAse III enzyme Drosha, partnering with DGCR8 (in vertebrates) or Pasha (in invertebrates), and transforming pri-miRNAs into shorter stem-loop-structured, double-stranded RNAs (dsRNAs) called precursor miRNAs (pre-miRNAs) (Denli, et al. (2004) *Nature* 432:231; Gregory, et al. (2004) *Nature* 432:235; Lee, et al. (2003) *Nature* 425:415). Pre-miRNAs are then transported from the nucleus to the cytoplasm and are processed by Dicer into mature miRNAs (Bernstein, et al. (2001) *Nature* 409:363; Grishok, et al. (2001) *Cell* 106:23-34; Hutvagner, et al. (2001) *Science* 293:834; Ketting, et al. (2001) *Genes Dev.* 15:2654; Yi, et al. (2003) *Genes Dev.* 17:3011). Mature miRNAs enter the effector complex, called the RNA-induced silencing complex (RISC), to target single-stranded complementary mRNAs for translational repression or mRNA degradation (Hammond (2006) *Curr. Opin. Genet. Dev.* 16:4-9; Hammond, et al. (2000) *Nature* 404:293; Hutvagner & Zamore (2002) *Science* 297:2056; Valencia-Sanchez, et al. (2006) *Genes Dev.* 20:515; Filipowicz (2005) *Cell* 122:17-20; Doench & Sharp (2004) *Genes Dev.* 18:504). It is estimated that miRNAs are involved in the regulation of about 30% of all genes and almost every genetic pathway (Hwang & Mendell (2006) *Br. J. Cancer* 94:776).

MicroRNAs play important roles in processes as diverse as normal development and cellular homeostasis (Bartel (2004) *Cell* 116:287-297; Plasterk (2006) *Cell* 124:877-881). Moreover, strong evidence suggests that they can function as oncogenes or tumor suppressors (Chan, et al. (2005) *Cancer Res.* 65:6029; Cimmino, et al. (2005) *Proc. Natl. Acad. Sci. USA* 102:139449; He, et al. (2005) *Nature* 435:828; Zhang, et al. (2006) *Proc. Natl. Acad. Sci. USA* 103:9136). For example, human miR-373 and 520C miRNAs have been shown to stimulate cancer cell migration and induce tumor cell invasion in vitro and in vivo. Mechanistically, the migration phenotype of miR-373 and miR-520C is explained by their suppression of CD44 expression. miR-373 and miR-520C inhibit CD44 expression through two sites at the 3'-UTR of CD44. Ectopic expression of CD44 restrains migration induced by miR-373 and miR-520C, while suppression of CD44 expression induces migration and metastasis (Huang, et al. (2008) *Nature Cell Biology* 10:202). Furthermore, a significant up-regulation of miR-373 expression is observed in clinical breast cancer primary and metastasis samples, wherein miR-373 expression is inversely correlated with CD44 expression in these tumors. While specific miRNA inhibition has been achieved by antisense nucleic acid approaches, effective delivery of such molecules is an issue (Meister, et al. (2004) *Mol. Cell.* 15:185).

SUMMARY OF THE INVENTION

The present invention is a method for identifying a microRNA modulator. The invention involves contacting a cell harboring a microRNA and a microRNA binding sequence, which is operably linked to a nucleic acid molecule encoding a reporter protein, with a test agent and determining whether the test agent increases or decreases the expression of the reporter protein thereby identifying a microRNA modulator. Modulators identified by this screening assay are also provided.

The present invention also embraces diazobenzene, indenoisoquinoline and cyclopentaphenanthrene miR-21 antagonists and methods for using the same to inhibit the activity of miR-21 microRNA and treat a disease or condition associated with miR-21.

BRIEF DESCRIPTION OF THE DRAWINGS

FIG. 4 shows changes in gene expression upon treatment with compound 2.

DETAILED DESCRIPTION OF THE INVENTION

Figure 1:
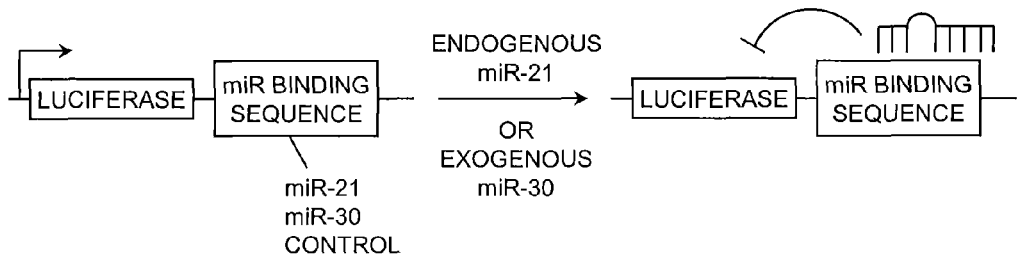
FIG. 1 depicts the instant miRNA assay employing luciferase under control of a 3' miRNA binding sequence. Endogenous miR-21 (HeLa cells) or exogenous miR-30A downregulate luciferase activity when paired with their specific binding sequence.

An assay for small molecule modulators of miRNA function has now been developed and used to identify highly selective miRNA modulators. As depicted in FIG. 1, the assay employs a miRNA binding sequence linked to a nucleic acid molecule encoding a reporter protein for use in monitoring changes in reporter protein expression upon exposure to test agents. By way of illustration, the assay was employed in the screening of >1000 small organic molecules for antagonistic activity toward the miR-21 microRNA and an initial hit was discovered which resulted in a 5-fold increase in reporter protein expression. Given the roles of microRNA in a number of cellular processes including normal development, cellular homeostasis and cancer, compounds that specifically modulate microRNA function find application in the treatment of diseases and conditions associated with microRNA, e.g., as chemotherapeutics for the treatment of cancers such as breast, ovarian, lung and brain cancer. Moreover, microRNA modulators can be employed in the research setting to analyze the biogenesis, degradation, and function of microRNAs.

Accordingly, the present invention is a method for identifying microRNA modulators. In one embodiment the microRNA modulator is an antagonist. In another embodiment, the microRNA modulator is an agonist. In accordance with this method, a cell harboring a microRNA and a microRNA binding sequence, which is operably linked to a nucleic acid molecule encoding a reporter protein, is contacted with a test agent and it is determined whether the test agent increases or decreases the expression of the reporter protein. As is conventional in the art, miRNA or microRNA refer to 19-25 nucleotide non-coding RNAs derived from endogenous genes that act as post-transcriptional regulators of gene expression. They are processed from longer (ca 70-80 nucleotide) hairpin-like precursors termed pre-miRNAs by the RNAse III enzyme Dicer. MicroRNAs assemble in ribonucleoprotein complexes termed miRNPs and recognize their target sites by antisense complementarity thereby mediating down-regulation of their target genes.

Any microRNA can be assayed in accordance with this invention. Indeed, the microRNA can be isolated from any cell including, *C. elegans, D. melanogaster, M. musculus* or *H. sapiens*. However, in particular embodiments, the microRNA is isolated from mammalian cells, desirably a human cell. Examples of human microRNA which can be assayed using the instant method include, but are not limited to, miR-17, miR-19a, miR-21, miR-30C, miR-31, miR-34b, miR-34c, miR-127, miR-136, miR-141, miR-142-3p, miR-142-5p, miR-143, miR-144, miR-145, miR-150, miR-200b, miR-200c, miR-221, miR-222, miR-373, miR-376a, miR-451, miR-486 and miR-520C.

A microRNA binding sequence is a nucleotide sequence, typically found in the 3'-untranslated region (UTR) of an mRNA, to which a microRNA binds to effect the down-regulation of a target mRNA. The selection of microRNA binding sequence for use in the invention will be dependent on the microRNA being assayed. While the microRNA and microRNA binding sequence may be 100% complementary, a microRNA binding sequences with less than 100% complementary to the microRNA can also be employed. For example, microRNA binding sequences which are 90% to 99% complementary to the microRNA are also embraced by the present invention. Examples of human microRNAs and their respective microRNA binding sequences are listed in Table 1.

TABLE 1

| microRNA | microRNA Binding Sequence 5'->3' | SEQ ID NO: |
|---|---|---|
| miR-143 | GAGCUACAGUGCUUCAUCUCA | 1 |
| miR-19a | UCAGUUUUGCAUAGAUUUGCACA | 2 |
| miR-188 | CCCUCCACCAUGCAAGGGAUG | 3 |
| miR-146a | AACCCAUGGAAUUCAGUUCUCA | 4 |

TABLE 1-continued

| microRNA | microRNA Binding Sequence 5'->3' | SEQ ID NO: |
|---|---|---|
| miR-206 | CCACACACUUCCUUACAUUCCA | 5 |
| miR-205 | CAGACUCCGGUGGAAUGAAGGA | 6 |
| miR-21 | UCAACAUCAGUCUGAUAAGCUA | 7 |
| miR-194 | UCCACAUGGAGUUGCUGUUACA | 8 |
| miR-150 | CACUGGUACAAGGGUUGGGAGA | 9 |
| miR-103 | UCAUAGCCCUGUACAAUGCUGCU | 10 |
| miR-144 | AGUACAUCAUCUAUACUGUA | 11 |
| miR-145 | AGGGAUUCCUGGGAAAACUGGAC | 12 |

A compendium of microRNA and respective microRNA binding sequences is available at the miRNA registry. See, e.g., Griffiths-Jones et al. (2006) *Nucl. Acids Res.* 34: D140-D144. In particular embodiments, the microRNA and microRNA binding sequence employed in the present assay are associated with a disease or condition, wherein an antagonist or agonist to the microRNA would be useful in preventing or treating the disease or condition. For example, the miR-17-92 cluster has been shown to be overexpressed in cancer cells and enhance cell proliferation (Hayashita, et al. (2005) *Cancer Research* 65:9628-9632). Similarly, miR-155 has been implicated as a human oncogene (Tam & Dahlberg (2005) *Genes, Chromosomes and Cancer* 45:211-212). Human miR-373 and miR-520C miRNAs have also been shown to stimulate cancer cell migration and induce tumor cell invasion in vitro and in vivo. Likewise, antisense studies of miR-21 in glioblastoma cell lines showed that this miRNA controls cell growth by inhibiting apoptosis, thereby demonstrating an oncogenic role for this miRNA (Clafre, et al. (2005) *Biochem. Biophys. Res. Commun.* 334:351-1358). Accordingly, such microRNAs and their respective microRNA binding sequences find particular use in the present assay.

To monitor binding between the microRNA and microRNA binding sequence, the microRNA sequence is operably linked to a nucleic acid molecule encoding a reporter protein. As used herein, the term "operably linked" refers to a linkage of nucleic acid elements in a functional relationship. A nucleic acid molecule encoding a reporter protein which is "operably linked" to a microRNA binding sequence, means that said microRNA binding sequence is in the correct location and orientation in relation to the coding sequence to control expression of the coding sequence upon binding by an microRNA. Certain embodiments of the invention embrace operably linking the microRNA binding sequence downstream (i.e., 3') of the reporter protein coding sequence. In particular, the microRNA binding sequence is located in the 3'-UTR of the mRNA encoding the reporter protein. However, in so far as target mRNAs have been shown to be repressed as efficiently by microRNA binding sequences in the 5'-UTR as in the 3'-UTR (see Lytle, et al. (2007) *Proc. Natl. Acad. Sci. USA* 104:9667-9672), other embodiments of the invention embrace positioning the microRNA binding sequence upstream of the reporter protein coding sequence, i.e., in the 5'-UTR.

As is conventional in the art, a reporter protein is a protein which produces a detectable signal when it is expressed. Reporter proteins of use in the invention can be autofluorescent or catalyze a reaction which produces a detectable product. Examples of such reporter proteins include, but are not limited to, green fluorescent protein (GFP), red fluorescent protein (RFP), yellow fluorescent protein (YFP), luciferase, beta-galactosidase, and beta-glucuronidase.

Generally, the nucleic acid molecule encoding the reporter protein will be in a vector for ease of manipulation and transformation. Any suitable vector, particular any suitable expression vector, can be employed including chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any system or vector which is able to maintain, propagate or express an mRNA to produce a protein in a host can be used. In this regard, the expression vector should contain a promoter upstream of the coding sequence to direct transcription (e.g., conditional or constitutive) of the mRNA encoding the reporter protein. Furthermore, the vector can contain other regulatory sequences such as polyadenylation signals and the like to control mRNA transcription and translation of the reporter protein. Such nucleic acid molecules can be inserted into an expression vector by any of a variety of well-known and routine techniques, such as, for example, those set forth in Sambrook et al., *Molecular Cloning, A Laboratory Manual*, 2nd Ed., Cold Spring Harbor Laboratory Press, Cold Spring Harbor, N.Y. (1989). Alternatively, a vector such as the pMIR-REPORT miRNA Expression Reporter Vector (Ambion, Austin, Tex.) can be used for inserting the microRNA binding sequence downstream of the luciferase coding sequence.

Cells of use in accordance with the present method can be selected for the expression of an endogenous microRNA or be genetically engineered using conventional methods to express exogenous microRNA. In either embodiment, said cell is said to harbor a microRNA. Cells of the invention are typically eukarotyic and preferably mammalian. Examples of suitable mammalian host cells include, but are not limited to CHO, COS, HeLa, C127, 3T3, BHK, and HEK 293 cells, which are well-known and commercially available in the art from sources such as the American Type Culture Collection (Manassas, Va.).

To carry out the claimed method, cells harboring a microRNA must also be transformed or transfected with the microRNA binding sequence operably linked to the nucleic acid molecule encoding the reporter protein. Generally, introduction of nucleic acids into mammalian cells can be effected by methods described in many standard laboratory manuals, such as Davis, et al., *Basic Methods in Molecular Biology* (1986) and Sambrook, et al., Molecular *Cloning: A Laboratory Manual*, (supra). Such methods include, for instance, calcium phosphate transfection, DEAE-dextran mediated transfection, transvection, microinjection, cationic lipid-mediated transfection, electroporation, transduction, scrape loading, ballistic introduction or infection.

Once a cell harbors both the microRNA and the microRNA binding sequence operably linked to a nucleic acid molecule encoding the reporter protein, the screening assay is carried out by contacting the cell with a test agent. Test agents which can be screened in accordance with the method of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic molecules, and purified or partially purified natural products. Examples of agent mixtures include, but are not limited to, extracts of prokaryotic or eukaryotic cells and tissues, as well as fermentation broths and cell or tissue culture supernates. In certain embodiments of this invention, the test agent is not a nucleic acid or nucleic acid molecule, e.g., not an antisense RNA, siRNA, or the like. In other embodiments, the test agent is a small organic molecule of less than ~2000 daltons.

Library screening can be performed as disclosed herein or in any format that allows rapid preparation and processing of multiple reactions. For in vitro screening assays, stock solutions of the test agents as well as assay components can be prepared manually and all subsequent pipeting, diluting, mixing, washing, incubating, sample readout and data collecting carried out using commercially available robotic pipeting equipment, automated work stations, and analytical instruments for detecting the signal generated by the assay. Examples of such detectors include, but are not limited to, luminometers, spectrophotometers, and fluorimeters, or any other device which can detect changes in reporter protein activity.

Upon detecting signals generated by the reporter protein it is determined whether the test agent increases or decreases the expression of the reporter protein as compared to a control. Such a determination can be carried out by comparing the signal produced by a cell contacted with a test agent to the signal produced by a control cell, e.g., a cell not contacted with a test agent or a cell contacted with the test agent but lacking a microRNA binding sequence. Agents that result in higher reporter protein signal are indicative of agents which antagonize the miRNA thereby increasing the expression of the reporter protein. In contrast, agents that result in a decrease in reporter protein signal compared to a control are indicative of agents which agonize the miRNA thereby decreasing the expression of the reporter protein.

By way of illustration, the instant assay was carried out screening small organic molecules for modulatory activity toward the microRNA miR-21. This screen identified several classes of compound which inhibited miR-activity as determined by an increase in luciferase activity. Compounds exhibiting miR-21 inhibitory activity included diazobenzenes, indenoisoquinolines and cyclopentaphenanthrenes:

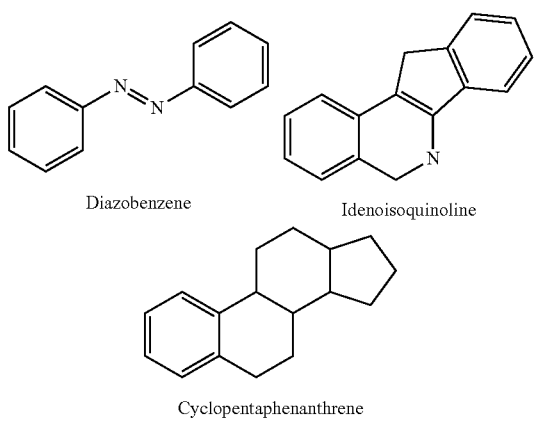

Thus, in accordance with methods for inhibiting the activity of miR-21, it is desirable that the antagonist employed has a core structure of a diazobenzene, indenoisoquinoline or cyclopentaphenanthrene. In this regard, the present invention embraces the diazobenzenes (i.e., Compounds 1, 2 and 3), indenoisoquinolines (i.e., Compounds 4 and 5) and cyclopentaphenanthrenes (i.e., Compounds 6, 7, 8, and estrone) disclosed herein, as well as derivatives and analogs thereof for use in methods for inhibiting miR-21 activity and treating or preventing a disease or condition associated with miR-21.

A derivative or analog of a diazobenzene, indenoisoquinoline or cyclopentaphenanthrene disclosed herein is a compound derived or obtained from a diazobenzene, indenoisoquinoline or cyclopentaphenanthrene, which contains the essential elements of the parent compound, but has had one or more atoms (e.g., halo, lower alkyl, hydroxyl, amino, thiol, or nitro), or group of atoms (e.g., amide, aryl, heteroaryl, allyl, or propargyl), replaced or added. Such replacements or substitutions can include substituent R groups and/or atoms of the core structure, e.g., replacing a carbon with a heteroatom such as a nitrogen, oxygen, or sulfur. In this regard, the compounds disclosed herein serve as lead compounds for creating a family of analogs with antagonistic activity toward mi-R21.

In one embodiment, a diazobenzene for use in inhibiting the activity of miR-21 is set forth herein in Formula I:

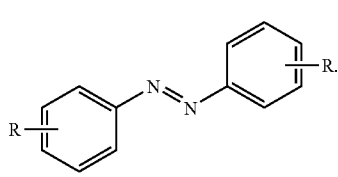

Formula I

In another embodiment, a indenoisoquinoline for use in inhibiting the activity of miR-21 is set forth herein in Formula II:

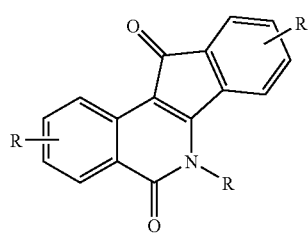

Formula II

In a further embodiment, a cyclopentaphenanthrene for use in inhibiting the activity of miR-21 is set forth herein in Formula III:

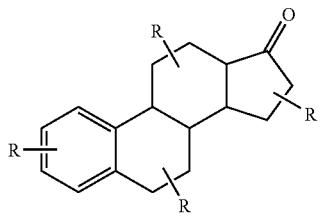

Formula III

In accordance with the compounds of Formulae I, II, and III, each R can independently be H, amino, hydroxyl (—OH), thiol (—SH), amide, aryl, heteroaryl, allyl, propargyl, alkyl (e.g., methyl, ethyl, propyl, butyl, etc.), silyl, halogen, or nitro (—NO$_3$), with the proviso that the compound of Formula I is not Compound 3, the compound of Formula II is not Compound 4, and the compound of Formula II is not Compound 6, 7, 8 or estrone.

As used herein, the term "amine" or "amino" is art-recognized and refers to both unsubstituted and substituted amines and salts thereof, e.g., a moiety that can be represented by

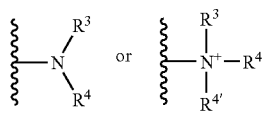

wherein $R^3$, $R^4$ and $R^{4'}$ each independently represent a hydrogen, aryl, heteroaryl, allyl or propargyl group, or $R^3$ and $R^4$ taken together with the N atom to which they are attached complete a heterocycle having from 4 to 8 atoms in the ring structure.

The term "amide", as used herein, refers to a group

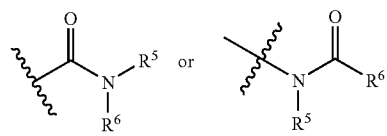

wherein $R^5$ and $R^6$ each independently represent a hydrogen or hydrocarbyl group, or $R^5$ and $R^6$ taken together with the N atom to which they are attached complete a heterocycle having from 4 to 8 atoms in the ring structure.

The term "aryl" is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, phenyl, substituted phenyl, hydroxy, hydroxyalkyl, alkoxy, aryloxy, alkoxyalkyl, haloalkyl, nitro, amino, alkylamino, acylamino, alkylthio, alkylsulfinyl, and alkylsulfonyl. Aryl groups having heteroatoms in the ring structure, are also included within the scope of the present invention and are referred to herein as heteroaryls. Exemplary aryl groups include phenyl, naphthyl, biphenyl, tetrahydronaphthyl, indanyl, 2-chlorophenyl, 3-chlorophenyl, 4-chlorophenyl, 4-fluorophenyl, 2-methylphenyl, 4-methoxyphenyl, 4-trifluoromethylphenyl, 4-nitrophenyl, and the like.

An allyl group is used herein to refer to a substituent that is or contains the unsaturated monovalent group CH$_2$=CHCH$_2$—.

The term "propargyl" is defined as $R^7$—C≡C—CH$_2$—, wherein $R^7$ is hydrogen, lower alkyl, haloalkyl, cycloalkyl, substituted or unsubstituted aryl, or substituted or unsubstituted heteroaryl.

As used herein, the term "alkyl" is defined to include straight chain and branched chain saturated hydrocarbon groups containing one to 16 carbon atoms, either substituted or unsubstituted. In particular embodiments, the alkyl is a "lower alkyl" which is defined herein as an alkyl group having one through six carbon atoms ($C_1$-$C_6$). Examples of lower alkyl groups include, but are not limited to, methyl, ethyl, n-propyl, isopropyl, isobutyl, tertiary butyl, isopentyl, n-butyl, neopentyl, n-hexyl, and the like.

The term "halogen" or "halo" is defined herein to include chlorine, fluorine, iodine, or bromine.

The term "silyl" generally refers to a silicon with one to three substitutions, e.g., alkyl and like.

The miR-21 antagonists identified herein, as well as antagonists of other microRNA identified using the instant screening assay find application in methods for inhibiting the activity of microRNAs. The methods involve contacting a cell which expresses the microRNA of interest (e.g., miR-21) with an effective amount of a microRNA antagonist (e.g., a diazobenzene, indenoisoquinoline or cyclopentaphenanthrene miR-21 antagonist) thereby inhibiting the activity of the microRNA. An effective amount of an antagonistic compound is an amount which reduces or decreases the activity of the microRNA by 10%, 20%, 30%, 40%, 50%, 60%, 70%, 80%, 90% or 100%. Such activity can be monitored by detecting the level of target mRNA or detecting the level of the protein product translated from the target mRNA.

In one embodiment, the microRNA being inhibited is miR-21 and the compound is a diazobenzene, indenoisoquinoline or cyclopentaphenanthrene. In another embodiment, the microRNA being inhibited is miR-21 and the compound is a compound of Formula I, Formula II or Formula III. In particular embodiments, the microRNA being inhibited is miR-21 and the compound is Compound 1, 2, 3, 4, 5, 6, 7, 8, or estrone.

Given the identified role of microRNA in various diseases and disorders, inhibiting the activity of a microRNA with a microRNA antagonist can be useful in selectively analyzing the biogenesis, degradation, and function of microRNAs as well as in preventing or treating diseases and disorders involving microRNAs, e.g., in the prevention or treatment of heart failure or cancers such as breast, ovarian, lung, colon, and brain cancer. In particular, miR-21 has been shown to be oncogenic in glioblastoma (Clafre, et al. (2005) supra) and therefore a miR-21 antagonist, such as the diazobenzenes, indenoisoquinolines and cyclopentaphenanthrenes disclosed herein, will be useful in the prevention or treatment of glioblastoma. In addition, miR-21 has been shown to contribute to myocardial disease by stimulating the ERK-MAP kinase signaling pathway in cardiac fibroblasts, wherein in vivo silencing of miR-21 in a mouse pressure-overload-induced disease model reduced cardiac ERK-MAP kinase activity, inhibited interstitial fibrosis and attenuated cardiac dysfunction (Thum, et al. (2008) *Nature* 456:980-4). Therefore, a miR-21 antagonist, such as the diazobenzenes, indenoisoquinolines and cyclopentaphenanthrenes disclosed herein, will be useful in the prevention or treatment of myocardial disease.

Accordingly, in one embodiment, the disease or disorder involves miR-21 and the compound is a diazobenzene, indenoisoquinoline or cyclopentaphenanthrene. In another embodiment, the disease or disorder involves miR-21 and the compound is a compound of Formula I, Formula II or Formula II. In particular embodiments, the disease or disorder involves miR-21 and the compound is Compound 1, 2, 3, 4, 5, 6, 7, 8, or estrone.

As indicated, agonists are also embraced by this invention, wherein said agonists are useful in selectively analyzing the biogenesis, degradation, and function of microRNAs as well as in preventing or treating diseases and disorders involving microRNAs.

Use of the modulators of the invention in the prevention or treatment of disease typically involves administering to a subject in need of treatment, i.e., a subject having or suspected of having a disease or condition which is caused by or associated with the overexpression or activity of a microRNA, a pharmaceutical composition containing an effective of a modulator identified in the screening method of the invention. In most cases this will be a human being, but treatment of agricultural animals, e.g., livestock and poultry, and companion animals, e.g., dogs, cats and horses, is expressly covered herein. The selection of the dosage or effective amount of a miRNA modulator is that which has the desired outcome of preventing (i.e., prophylactic treatment), reducing or reversing at least one sign or symptom of the disease or disorder being treated. Such signs or symptoms are well-known in the art and can be monitored by the skilled clinician upon commencement of treatment. Efficacy of a miRNA modulator can be determined using conventional preclinical and clinical approaches. Examples of preclinical models for the prevention and treatment of cancer or heart failure are disclosed herein.

Modulators of the present invention can be used alone or in combination with other agents, such as cancer chemotherapeutic agents, in the treatment of disease. Thus, in particular embodiments, the present invention embraces combining an effective amount of an antagonist identified in the screening method of the invention with one or more chemotherapeutic agents or antiproliferative agents. The drug combination can be included in the same or multiple pharmaceutical compositions. In addition, the individual drugs can be administered simultaneously or consecutively (e.g., immediately following or within an hour, day, or month of each other). Examples of antiproliferative agents which can be used in combination with an antagonist of the invention include, but are not limited to, antimetabolites, such as methotrexate, 5-fluorouracil, gemcitabine, cytarabine, pentostatin, 6-mercaptopurine, 6-thioguanine, L-asparaginase, hydroxyurea, N-phosphonoacetyl-L-aspartate (PALA), fludarabine, 2-chlorodeoxyadenosine, and floxuridine; structural protein agents, such as the vinca alkaloids, including vinblastine, vincristine, vindesine, vinorelbine, paclitaxel, and colchicine; agents that inhibit NF-kappaB, such as curcumin and parthenolide; agents that affect protein synthesis, such as homoharringtonine; antibiotics, such as dactinomycin, daunorubicin, doxorubicin, idarubicin, bleomycins, plicamycin, and mitomycin; hormone antagonists, such as tamoxifen and luteinizing hormone releasing hormone (LHRH) analogs; nucleic acid damaging agents such as the alkylating agents mechlorethamine, cyclophosphamide, ifosfamide, chlorambucil, dacarbazine, methylnitrosourea, semustine (methyl-CCNU), chlorozotocin, busulfan, procarbazine, melphalan, carmustine (BCNU), lomustine (CCNU), and thiotepa; the intercalating agents doxorubicin, dactinomycin, daurorubicin and mitoxantrone; the topoisomerase inhibitors etoposide, camptothecin and teniposide; antibodies such as the anti-HER2 monoclonal antibody; and the metal coordination complexes cisplatin and carboplatin.

Pharmaceutical compositions containing modulators of the invention alone, or in combination with other agents, can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body.

Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The modulators of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

EXAMPLE 1 miRNA Inhibitor Screening Assay

MicroRNA miR-21 was selected as a target miRNA due to its involvement as an anti-apoptotic factor in cancer cells and its elevated levels in various cancers such as breast, ovarian, and lung cancer as well as glioblastoma (Chan, et al. (2005) *Cancer Res.* 65:6029). Lentiviral reporter constructs for miRNA activity were assembled by introducing the complementary sequences of mature miR-21 (5'-UAG CUU AUC AGA CUG AUG UUG A-3'; SEQ ID NO:13), miR-30A (5'-CUU UCA GUC GGA UGU UUG CAG C-3'; SEQ ID NO:14) as a specificity control, and a linker sequence (a previously present multiple-cloning site with no detectable recognition by natural miRNAs) downstream of a luciferase reporter gene as a negative control (FIG. 1).

Luc-miR-21, Luc-miR-30A, and Luc-linker (control) were, by viral infection, introduced into HeLa cells, which express high levels of miR-21, but only low levels of miR-30A (Cheng, et al. (2005) *Nucl. Acids Res.* 33:1290).

Figure 2:
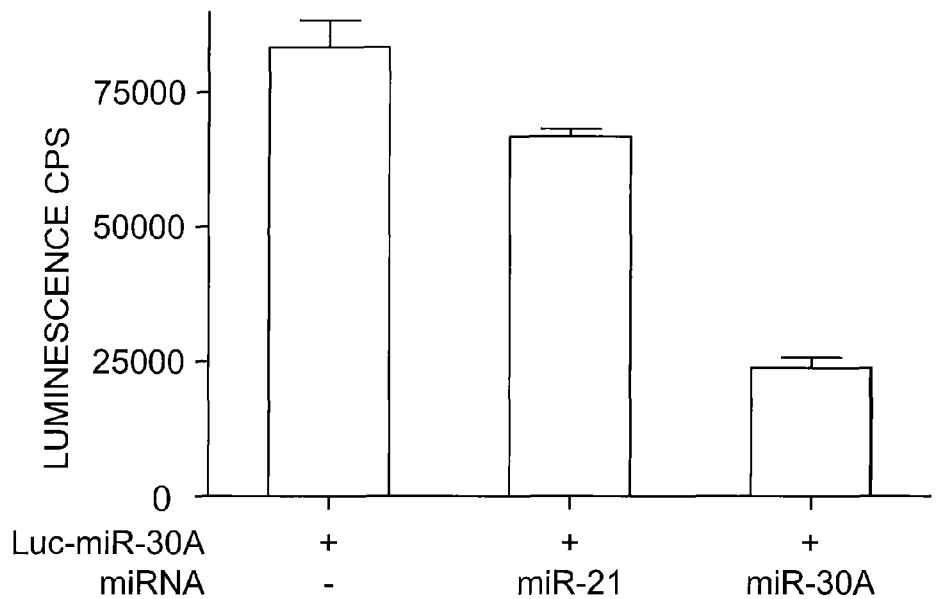
FIG. 2 shows the results of analyses which were conducted to demonstrate the specificity of the miR-30A reporter for miR-30A.

The specificity of the reporter system was tested by assaying cells which contained both the Luc-miR-30A reporter and a construct expressing exogenous miR-30. These cells displayed a much lower luciferase signal than cells with a mismatched Luc-miR-30A reporter/miR-21 combination (FIG. 2). This demonstrates that the Luc-miR-21 and Luc-miR-30A reporters are specific and only react to miR-21 and miR-30, respectively.

The ability to detect endogenous miRNAs was proven by the fact that the Luc-miR-21 reporter, stably introduced into HeLa cells, led to a 90% decrease in luciferase signal in comparison to the control luciferase-linker construct, visualizing the high level of matching endogenous miR-21 expression in HeLa cells. By comparison, the miR-30A reporter displayed only a modest decrease since HeLa cells express only low levels of endogenous miR-30A. These analyses indicate that the luciferase-complementary sequence plasmids serve as sensors to detect the presence of specific mature miRNAs (e.g., miR-21 and miR-30A, see FIG. 1) and therefore any perturbation of miRNA activity by small molecules in host cells.

EXAMPLE 2

Identification of miR-21 Antagonists

To illustrate the method of the present invention, a primary screen of >1000 compounds was conducted. The library was composed of a collection of novel compounds and the Library of Pharmacologically Active Compounds (LOPAC library, Sigma-Aldrich, St Louis, Mo.). All compounds were stored at a 10 mM concentration in DMSO to keep the DMSO concentration in the actual screen at 0.1% thereby minimizing toxicity. HeLa cells stably expressing the miR-reporter were treated with DMSO ranging from 0.1-1%. Luciferase signals were determined 48 hours after the treatment.

HeLa cells (2500 cells) were plated in each well of 384-well plate 24 hour before the addition of compounds. Compounds at 10 μM final concentration were added to each well. Luciferase signal were determined 48 hours after compound treatment. Using this screening assay, compound 1 was identified as a miR-21 antagonist.

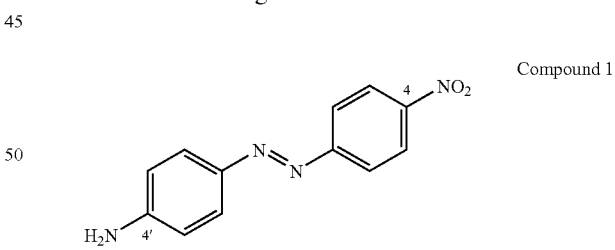

Compound 1

Figure 3:
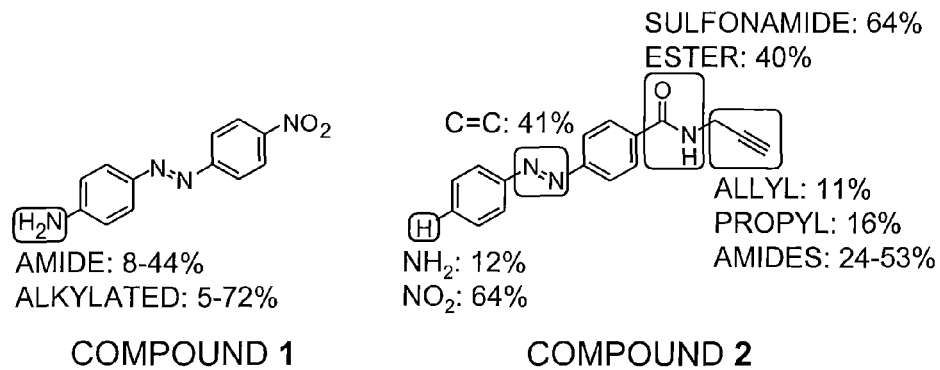
FIG. 3 summarizes structure-activity analysis of compounds 1 and 2. Percentages indicate loss in activity with the indicated modification.

This diazobenzene led to an increase of the luciferase signal by 251% compared to untreated cells (the DMSO control had no effect on the luciferase signal). Through several rounds of screening and structural modification, a preliminary structure-activity relationship was developed. Chemical modifications of the amino group in Compound 1 through acylation and alkylation led to diminished activities. However, subsequently conducted iterations of chemical modification and screening of more broadly modified molecules containing a diazobenzene core structure (FIG. 3) delivered the highly active compound 2 ((E)-4-(Phenyldiazenyl)-N-(prop-2-ynyl)benzamide; 5-fold increase of the luciferase signal at 10 μM).

Compound 2

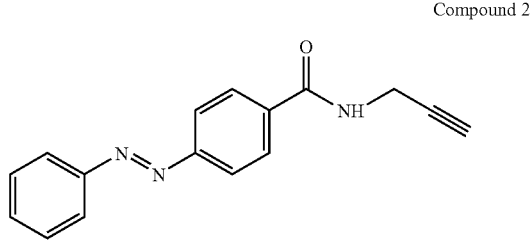

Modification of Compound 2 through introduction of an amino or nitro group in the 4' position led to 12% or 64% reduced activity, respectively. Other investigated amide groups led to a loss of activity (24-53%), whereas allyl and propyl groups showed 11% and 16% lower activity, respectively. Additionally, an exchange of the amide for a sulfonamide delivered compounds with no activity and the styrene analog of compound 2 had a 40% lower activity. Thus, compound 2 was the most effective small molecule inhibitor of microRNA miR-21 of those tested. This molecule increased the luciferase signal by 485% at a 10 μM concentration. The increase of luciferase signal was concentration dependent, revealing an $EC_{50}$ of 2 μM.

Figure 4A:
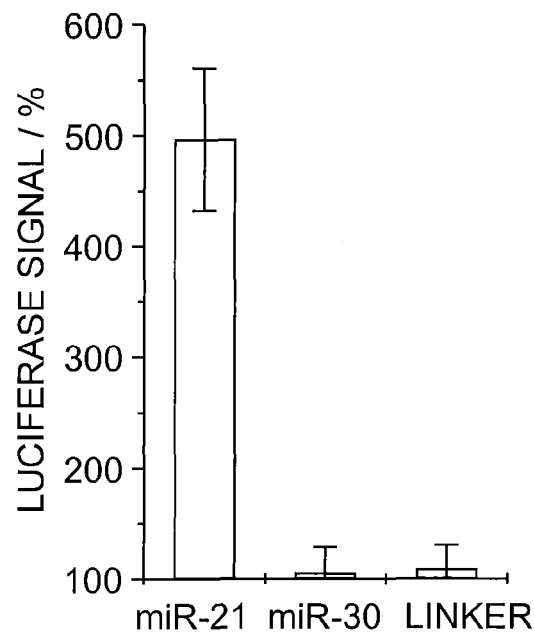
FIG. 4A shows changes in luciferase signal of cells treated with compound 2 (10 µM) relative to a DMSO control. The diazobenzene 2 is specific for miR-21, since it does not affect general luciferase expression or miR-30.

The diazobenzene 2 is specific to the miRNA pathway and does not increase the luciferase signal through a non-miRNA related mechanism, since it did not affect the luciferase signal in HeLa cells expressing the Luc-Linker control harboring a miRNA target sequence (FIG. 4A). It was subsequently determined whether Compound 2 was a specific inhibitor of miR-21 or whether it could interfere with the general miRNA biogenesis pathway. Thus, HeLa cells stably expressing both the miR-30 luciferase reporter construct and miR-30 were treated with Compound 2. In this case, no increase of the luciferase signal was detected (FIG. 4A), demonstrating that Compound 2 possesses a degree of specificity toward miR-21 and does not have a general effect on the common biogenetic pathway of miRNAs.

Figure 4B:
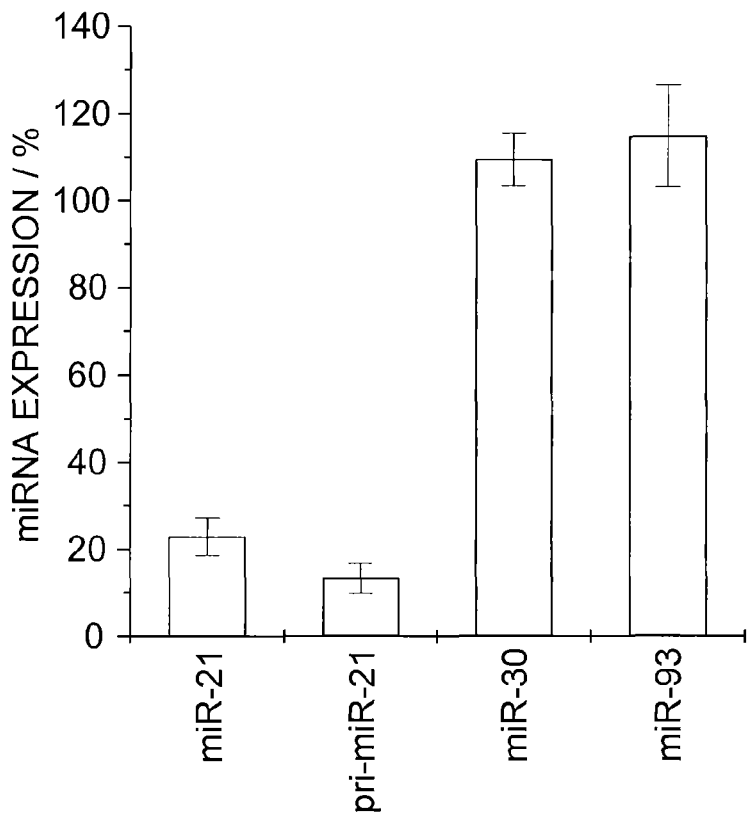
FIG. 4B shows miRNA levels in cells treated with compound 2 (10 µM) relative to a DMSO control, as determined by RT-PCR. miR-93 and miR-30 were used as endogenous and exogenous controls, respectively. All experiments were conducted in triplicate.

Quantitative RT-PCR assays were conducted in order to further validate the efficacy and specificity of Compound 2 (FIG. 4B). It was found that levels of the stably expressed, exogenous mature miR-30 and the randomly selected, endogenous mature miR-93 were not reduced by treatment with compound 2 (relative to DMSO) (FIG. 4B). This confirmed the specificity of Compound 2 for miR-21, the expression of which was reduced by approximately 67% to 78% compared to the DMSO control in HeLa cells. Furthermore, not only was the level of the mature miR-21 reduced, but also that of the primary miR-21 (pri-miR-21) sequence (by 87% as determined by using quantitative real-time RT-PCR primers selective for pri-miR-21 but not mature or precursor miR-21) (FIG. 4B). These results indicate that Compound 2 is selectively targeting the transcription of miR-21 but not downstream processes of the miRNA pathway.

The effect of Compound 2 on the expression level of four additional genes (E-cadherin, ID1, RAP1A, and Fibronectin) was also analyzed in the original HeLa cell line and three additional cell lines (MCF-7, A172, and MDA-MB-231 cells) by quantitative RT-PCR. Changes in gene expression were not significant, indicating that Compound 2 has no general effect on RNA biogenesis.

In addition to the experiments conducted in HeLa cells, quantitative RT-PCR experiments were performed for primary miR-21, mature miR-21, mature miR-30, and mature miR-93 in three additional cell lines which endogenously express these miRNAs, namely human breast cancer cell lines MDA-MB-231 and MCF-7, and human glioblastoma cell line A172. As with HeLa cells, Compound 2 suppressed both the primary and the mature miR-21 in all cell lines, but had no effect on miR-30 and miR-93. These experiments additionally validate the level of specificity and efficacy of Compound 2 as a miR-21 pathway inhibitor across several cell lines.

To further demonstrate the use of the screening assay of the invention, additional chemical modifications of compound 1 were prepared and screened. In addition, other libraries of compounds were screened for inhibitory activity as compared to compound 2. Table 2 provides the structure of compounds exhibiting pronounced inhibitory activity against miR-21, as well as the activity of compounds in the luciferase assay and RT-PCR assays to determine specificity.

TABLE 2

| Compound Structure | Luciferase Assay | miR-21 RT PCR* | miR-30 RT PCR* | miR-93 RT PCR* |
| --- | --- | --- | --- | --- |
| 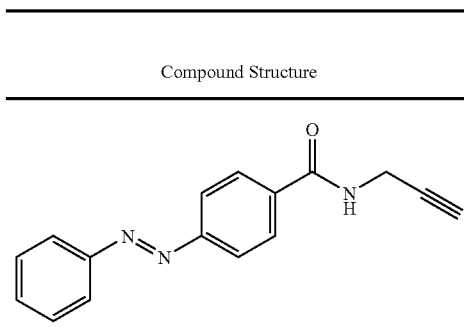 <br> 2 | 4.83 | 22% | 110% | 115% |
| 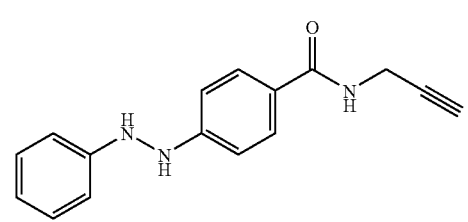 <br> 3 | 3.67 | 39% | 85% | 56% |

TABLE 2-continued

| Compound Structure | Luciferase Assay | miR-21 RT PCR* | miR-30 RT PCR* | miR-93 RT PCR* |
|---|---|---|---|---|
| 4[a] | 3.12 | 12% | 136% | 116% |
| 5 | 2.92 | ND | ND | ND |
| 6[b] | 3.34 | 34% | 73% | 83% |
| 7[b] | 3.04-3.87 | ND | ND | ND |
| 8[c] | 3.50 | ND | ND | ND |

TABLE 2-continued

| Compound Structure | Luciferase Assay | miR-21 RT PCR* | miR-30 RT PCR* | miR-93 RT PCR* |
|---|---|---|---|---|
| 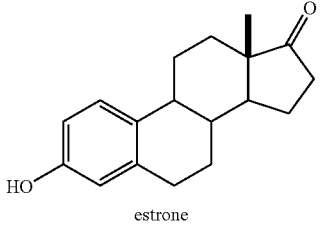 estrone | 2.76 | ND | ND | ND |

ND, not determined.
*% Decrease as compared to DMSO control.
<sup>a</sup>Strumberg, et al. (1999) J. Med. Chem. 42:446-457.
<sup>b</sup>Holt, et al. (1990) J. Med. Chem. 33:937-942; WO 2004106358.
<sup>c</sup>Enginar, et al. (2005) J. Radioanal. Nuclear Chem. 264:535-539; WO 2004106358.

EXAMPLE 3

Synthesis of the Diazobenzene 2

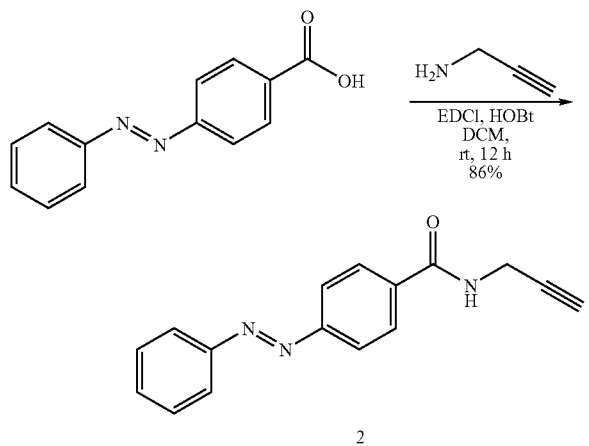

4-Phenylazobenzoic acid (30 mg, 0.133 mmol) was dissolved in DCM (1 mL), followed by the addition of 1-ethyl-3-(3'-dimethylaminopropyl)carbodiimide (42 mg, 0.22 mmol) and hydroxybenzotriazole (21 mg, 0.15 mmol). Propargylamine (15 mg, 0.27 mmol) was added and the reaction was stirred at room temperature for 12 hours. The reaction was quenched with water (5 mL) and extracted with DCM (3×5 mL). The organic layer was dried with sodium sulfate, concentrated and purified by silica gel chromatography (2:1 hexane/ethyl acetate) to yield an orange solid (29 mg, 0.11 mmol, 86%). $^1$H NMR (400 MHz, CDCl$_3$) δ 7.98-7.92 (m, 6H), 7.57-7.49 (m, 3H), 6.46 (bs, 1H), 4.29 (dd, $J_1$=2.4 Hz, $J_2$=4.8 Hz, 2H), 2.13 (t, J=2.4, 1H); $^{13}$C NMR (75 MHz, CDCl$_3$) δ 166.6, 154.6, 152.7, 135.6, 131.9, 129.4, 128.3, 123.4, 123.2, 79.5, 72.4, 30.2. HRMS Calcd for C$_{16}$H$_{14}$N$_3$O (MH$^+$): 264.1131, Found: 264.1135.

EXAMPLE 4

Cell Culture and RT-PCR Methods

Human Breast cancer cell lines MDA-MB-231 and MCF-7, Human glioblastoma cell line A172, and human cervical cancer cell line HeLa (obtained from American Type Cell Collection, Manassas, Va.) were grown in DMEM media (Mediatech, Manassas, Va.) supplemented with 10% fetal bovine serum, glutamine (2 mM), penicillin (100 units/ml), and streptomycin (100 μg/ml, Invitrogen). All cells were incubated at 37° C. in a humidified chamber supplemented with 5% CO$_2$.

Total RNA was extracted from HeLa, A172, MCF7 and MDA-MB-231 cells treated with DMSO or the small molecule inhibitor using TRIZOL total RNA isolation reagent (Invitrogen), according to the manufacturer's instructions. cDNA was synthesized from total RNA using specific mature miRNA primers (miR-21, miR-30 and miR-93 kits from Applied Biosystems) or random hexamers with High Capacity cDNA Reverse Transcription Kit and TAQMAN MicroRNA (Applied Biosystems), according to the manufacturer's instructions. The reactions were incubated in a thermal cycler for 30 minutes at 16° C., 30 minutes at 42° C., 5 minutes at 85° C. and then held at 4° C. Real-time PCR was performed using an Applied Biosystems 7500 Fast Real Time PCR system with specific mature miRNA primers from respective kits and TAQMAN Universal PCR Master Mix, no AMPERASE UNG (Applied Biosystems). To determine the level of primary miR-21 expression, primers were designed using Primer Express v3.0 Software (Forward primer, 5'-TTT AAT GGC CTT GCA CTC TTC TT-3' (SEQ ID NO:15); Reverse primer, 5'-TTT GTT CCA GTA TTA GGA GCT GTT TTT-3' (SEQ ID NO:16)) and real-time PCR was performed with SYBR GREEN Jumpstart Taq READYMIX (Sigma). The reactions were incubated in a 96-well plate at 95° C. for 10 minutes followed by 40 cycles of 15 seconds at 95° C. and 1 minute at 60° C.

The primers for the control genes (E-cadherin, ID1, RAP1A, and Fibronectin) used in this study were also designed using Primer Express v3.0 Software (ID1: forward 5'-CGA CAT GAA CGG CTG TTA CTC A-3' (SEQ ID NO:17), reverse 5'-TTG CTC ACC TTG CGG TTC T-3' (SEQ ID NO:18); E-cadherin: forward 5'-AAA TCT GAA AGC GGC TGA TAC TG-3' (SEQ ID NO:19), reverse 5'-CGG AAC CGC TTC CTT CAT AG-3' (SEQ ID NO:20); Fibronectin: forward 5'-CCG TTG GAA GGA AGC TAC CA-3' (SEQ ID NO:21), reverse 5'-CGT ACT GCT GGA TGC TGA TGA-3' (SEQ ID NO:22); RAP1A: forward 5'-CTG AGC CAG ATT ACA GGA ATG AAG-3' (SEQ ID NO:23), reverse 5'-GAA CTT GTG CAA ACC AAT ATA AGA TCT AA-3' (SEQ ID NO:24)) and experiments were performed as described above. The genes RNU-19 and GAPDH were used as endogenous controls, and the data was normalized to those endogenous controls. The relative expression level was calculated using the comparative $C_t$ method. The average of two independent analyses for each gene and sample was calculated.

EXAMPLE 5

Cell Viability Assays and Synergistic Drug Combinations

To further demonstrate the efficacy of the compounds of the invention for use in the prevention or treatment of cancer, cell viability assays were conducted. In these assays, A172 cells (glioblastoma cells) were contacted with a miR-21 inhibitor either alone or in combination with a conventional antiproliferative agent (i.e., 5-fluorouracil or curcumin). At the concentrations indicated, no toxic effects on HEK293T (human embryonic kidney) cells were observed. The results of this analysis are presented in Table 3.

TABLE 3

| | | Cell Viability | | |
|---|---|---|---|---|
| | | | A172 Cells | |
| Compound* | HEK293T Cells | Compound | Compound + 5FU (0.5 µM) | Compound + Curcumin (10 µM) |
| 2 | 98% | 84% | 8% | 12% |
| 3 | 95% | 75% | 52% | 56% |
| 4 | 98% | 66% | 62% | 54% |
| 5 | 79% | 70% | 45% | 40% |
| 6 | 97% | 71% | 47% | 39% |
| 7 | 86% | 87% | 54% | 43% |
| 8 | 89% | 100% | 78% | 57% |
| Estrone | 85% | ND | ND | ND |

*10 µM Compound.

Figure 5A:
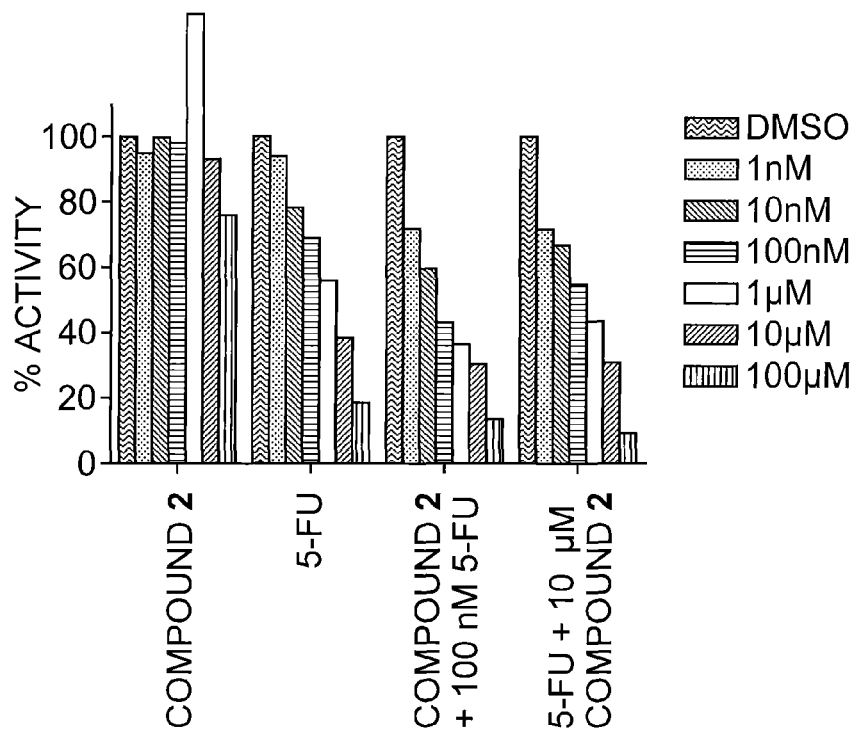
FIG. 5 shows the synergistic effect of compound 2 with 5-FU (FIG. 5A) and curcumin (FIG. 5B) on cell proliferation of colon cancer HCT116 cells. The % activity indicates % live cell activity.
Figure 5B:
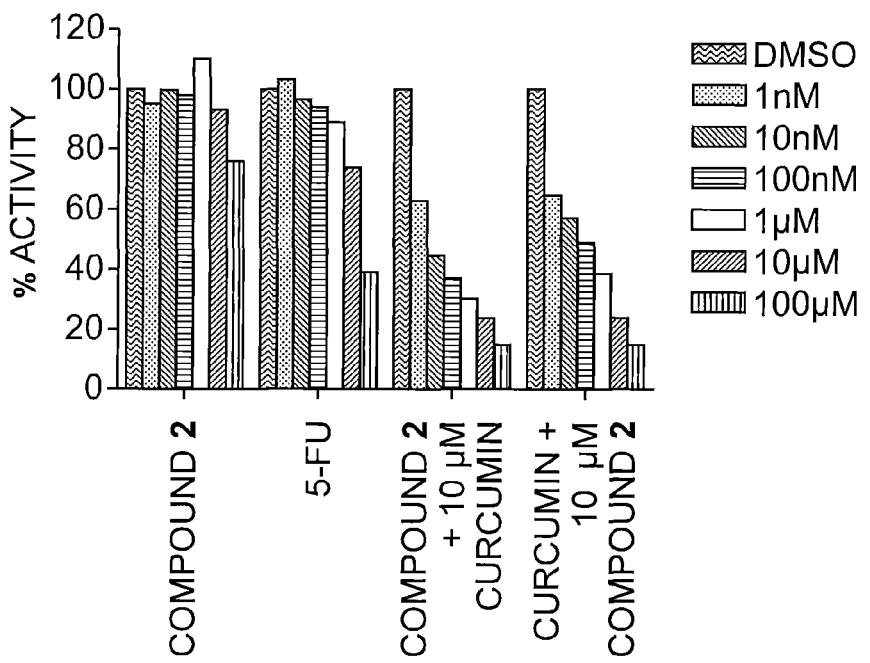
Figure 6A:
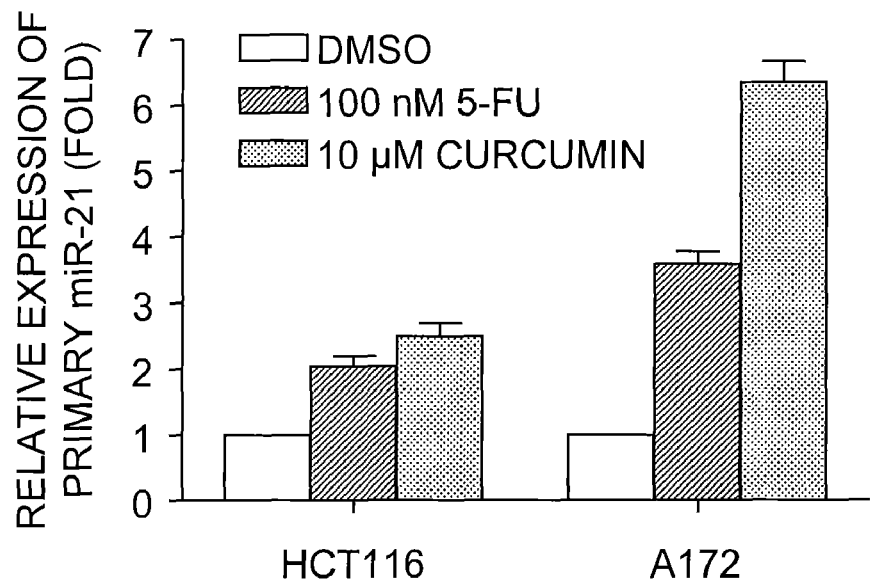
FIG. 6 shows that 5-FU and Curcumin treatment increase primary (FIG. 6A) and mature (FIG. 6B) miR-21 expression in colon cancer HCT116 cells and glioblastoma A172 cells.
Figure 6B:
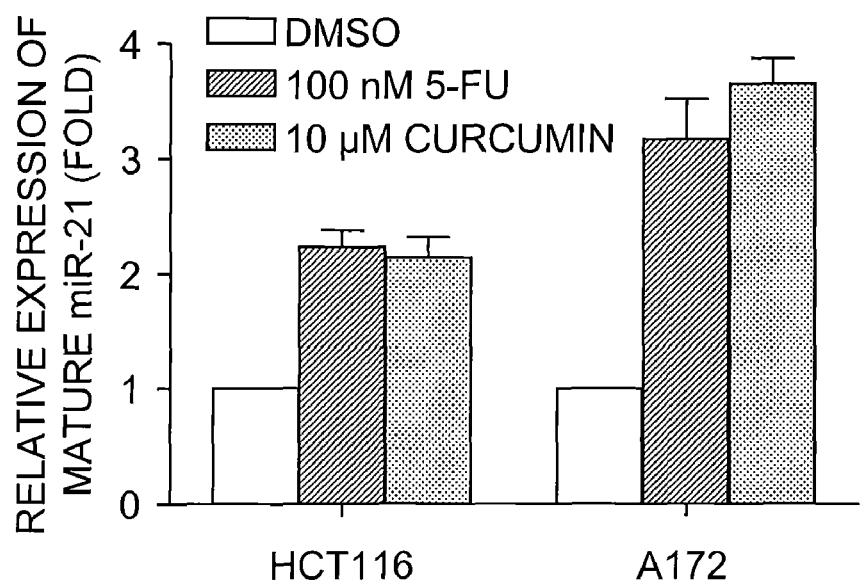

In addition to A172 cells, the combination of compound 2 with 5-FU (FIG. 5A) or Curcumin (FIG. 5B) was found to synergistically decrease the proliferation of HCT116 colon cancer cells. Moreover, as show in FIG. 6, 5-FU and Curcumin treatment increased the primary (FIG. 6A) and mature (FIG. 6B) miR-21 expression in HCT116 colon cancer cells and A172 glioblastoma cells.

EXAMPLE 6

Efficacy in a Mouse Model of Cancer

Efficacy of compounds identified in the screening assay of the invention can be determined using any conventional model. For example, antagonists of microRNA associated with cancer (e.g., miR-21, microRNA of the miR-17-92 cluster, miR-155, miR-373 and miR-520C) can be screened in a mouse xenograft model of cancer wherein the compounds are administered alone or in combination with a conventional antiproliferative agent (e.g., 5-FU or curcumin) either prior to or after tumor formation.

The pharmacokinetics of the compounds is first analyzed to determine distribution and metabolism in the mouse model. Mice are injected with the compounds either intraperotoneally (i.p.) or intravenously (i.v.). Serum from the mice is collected. The distribution and concentration of the compounds in the serum is determined by LC-MS.

A lentiviral construct capable of expressing luciferase is introduced, by viral infection, into various cancer cells including colon cancer cells such as HCT116, glioblstoma cells such as A172; and breast cancer cells such as MCF7 and other cancer cells in which miR-21 is expressed. Cancer cells stably expressing luciferase are injected orthotopically or subcutaneously into SCID mice. The SCID mice transplanted with tumor cells are treated with either a compound of the invention; an antiproliferative agent (e.g., 5-FU or curcumin); a combination of a compound of the invention and an antiproliferative agent at various dosages; or controls, by intraperitoneal, intravenous, local or orthotopic injection. The dosage regimens and interval of the treatment will depend on the pharmacokinetic results. Treatment can be started either at day 0, or 1 week or 2 weeks after tumor cell transplantation. Tumor growth is monitored and measured with a suitable optical imaging technology (e.g., Xenogen IVIS system; Xenogen Corporation, Hopkinton, Mass.) once every week. See Huang, et al. (2008) *Nat. Cell Biol.* 10:202-210; Gumireddy, et al. (2007) *Proc. Natl. Acad. Sci. USA* 104: 6696-6701. The tumor size of the compound-treated mice and mock-treated mice is compared to determine the efficacy of the compounds.

It is expected that miR-21 antagonist administration will reduce tumor size and/or metastasis; or prevent tumor growth and/or metastasis thereby demonstrating efficacy of a miR-21 antagonist in the prevention and treatment of cancer. In addition, it is expected that the co-administration of a miR-21 antagonist and an anticancer agent will have a synergistic effect on reducing tumor size and/or metastasis.

EXAMPLE 7

Efficacy in a Mouse Model of Myocardial Disease

To demonstrate that mi-R21 antagonists can prevent or treat myocardial disease, an established transverse aortic constriction (TAC) model (Rockman, et al. (1991) *Proc. Natl Acad. Sci. USA* 88:8277-8281; Buitrago, et al. (2005) *Nature Med.* 11:837-844), or isoproterenol-induced cardiac disease model (Thum, et al. (2008) supra) can be employed.

To demonstrate uptake, the antagonist can be fluorescently labeled with an appropriate dye, and uptake into cardiac fibroblasts and cardiomyocytes can be measured in vitro. In addition, labeled antagonist can be injected intravenously by a jugular vein catheter and staining of the left ventricular myocardium can be determined.

In the TAC model, a jugular vein catheter is inserted in male C57/BL6 mice (10-12 weeks old) before TAC is performed. Twenty-four hours (prevention study) or three weeks (therapy study) post-TAC, miR-21 antagonist or phosphate-buffered saline (PBS) is injected daily for three days through the jugular vein catheter.

In the isoproterenol-induced cardiac disease model, animals are subjected to infusion with isoproterenol by subcutaneously implanted osmotic minipumps (30 mg isoproterenol per gram per day). As with the TAC model, miR-21 antagonist or PBS is administered before (prevention study) or after (therapy study) isoproterenol infusion.

Cardiac miR-21 expression is monitored by northern blot and/or real-time polymerase chain reaction (PCR) analysis. Changes in MAP kinase activation are measured and the expression of genes encoding collagens and extracellular matrix molecules that are highly upregulated during cardiac fibrosis is monitored. Furthermore, interstitial fibrosis, cardiomyocyte size, heart weight, and left ventricular dilatation are measured at appropriate intervals after TAC or isoproterenol infusion.

It is expected that miR-21 antagonist administration will provide significant attenuation of the impairment of cardiac function as well as regression of cardiac hypertrophy and fibrosis thereby demonstrating efficacy of a miR-21 antagonist in the prevention and treatment of myocardial disease.

What is claimed is:

1. An miR-21 antagonist having the structure of compound 2:

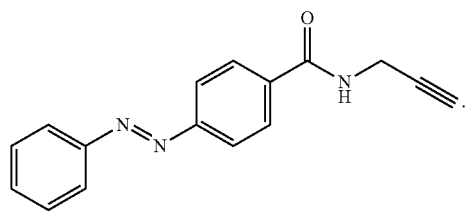

Compound 2

2. A pharmaceutical composition comprising the miR-21 antagonist having the structure of compound 2:

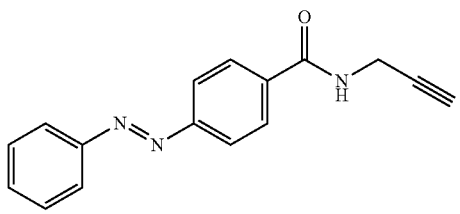

Compound 2 in admixture with a pharmaceutically acceptable carrier.

* * * * *